United States Patent [19]

Davidson

[11] Patent Number: 4,916,942
[45] Date of Patent: Apr. 17, 1990

[54] NOTCH GAUGE TOOL

[76] Inventor: Leonard W. Davidson, 5111 Bentley Dr., Delta, Canada

[21] Appl. No.: 371,565

[22] Filed: Jun. 26, 1989

[51] Int. Cl.$^4$ ............................................. G01M 15/00
[52] U.S. Cl. .................................... 73/119 R; 415/118
[58] Field of Search .............. 73/119 R, 116; 415/118

[56] References Cited

U.S. PATENT DOCUMENTS

| 4,741,203 | 5/1988 | Willaman et al. ...................... 73/116 |
| 4,741,205 | 5/1988 | Keller ..................................... 73/116 |

*Primary Examiner*—Jerry W. Myracle
*Attorney, Agent, or Firm*—Townsend and Townsend

[57] ABSTRACT

A tool and method for measuring turbine blade outer shroud notch wear in situ in a turbine having multiple stages of turbine blades, each stage being arranged in a circular array. The tool comprises a longitudinal member having first and second ends. A gauge pin for applying a separating force between two adjacent turbine blades is affixed adjacent the first end. A positioning member is mounted about the longitudinal member intermediate the first and second ends and a driving site is located adjacent the second end. The tool is used by inserting the first end of the longitudinal member through a first outer stage of blades and into the interior of the turbine such that the positioning member abuts the first outer stage of blades to place the gauge pin between two adjacent blades of an interior stage of blades. A torque force is applied to the tool at the driving site to separate the adjacent blades. A measure of the magnitude of the force required to separate the blades serves as an indication of outer shroud notch wear.

9 Claims, 1 Drawing Sheet

NOTCH GAUGE TOOL

FIELD OF THE INVENTION

This invention relates to a tool and method for measuring turbine blade outer shroud notch wear in a jet engine. It is particularly useful for measuring shroud notch wear in the Pratt and Whitney JT8D engine used in the Boeing 727, 737 and Douglas DC9 or MD 80 series of aircraft.

BACKGROUND OF THE INVENTION

Turbine rotors in modern jet engines and other turbine equipment generally comprise a circular array of blades extending outwardly from a rotatable shaft, the outer ends of the each blade being formed into outer shroud portions that interfit with the shroud portions of adjacent blades to create an annulus about the blades. The shroud portions are dimensioned to interfit together along joint lines called notches such that the shroud portions provides a tight external ring about the blades.

The tool and method of the present invention was developed particularly to address the problem of measuring shroud notch wear in Pratt & Whitney JT8D engines. These engines experience wear of the 92 third stage turbine blade outer shroud notches. If undetected the wear will result in failure of one or more blades and consequent damage to the downstream turbine components. Repair costs for this type of failure can exceed $300,000.

The engine manufacturer's recommendation to avoid this type of failure is to dismantle the turbine section after a set period of service to physically measure wear on the blades. Dismantling and examining of several engines should provide guidance for the degree of wear in other engines, but experience has shown that the wear rate of the notches is random. Some engines may be in danger of failure before a shop visit is due while other engines are able to continue in service long after the scheduled service period before notch wear reaches a critical state.

At present, due to the random nature of the shroud notch wear a lot of engines are dismantled unnecessarily. Since an engine shop dismantling and examination of the third stage turbine blades can cost over $100,000, there is obviously a need for a tool or method that will allow for testing of shroud notch wear without dismantling an engine at great expense.

Prior art methods for measuring wear in turbine blades are known. For example, U.S. Pat. No. 4,741,205 to Keller teaches a method of measuring shroud wear on the integrally shrouded rotating blades of a steam turbine. This method involves pre-forming special wedge notches in the shroud portions adapted to accept a wedge member that is used to apply a wedging force to move two adjacent shroud portions apart. The distance the shroud portions are moved apart is measured and provides an indication of wear on the shroud portions. This process requires that special wedging notches be formed in the rotor blades. These wedge notches are used only for measuring shroud portion wear and are a completely different item from the standard notches found in the shroud portions of the Pratt and Whitney JT8D jet engine. Keller's method therefore involves modifying an existing shroud design. In addition, it is necessary that the turbine be completely dismantled so that the distance between shroud portions can be measured as they are wedged apart.

SUMMARY OF THE INVENTION

There is a need for a tool and a method of measuring shroud notch wear that can be used without dismantling an engine and that does not involve modifying the existing shroud portion structure.

Accordingly, the present invention is a tool for measuring turbine blade outer shroud notch wear in situ in a turbine having multiple stages of turbine blades, each stage being arranged in a circular array comprising:

a longitudinal member having first and second ends;

means for applying a separating force between two adjacent turbine blades at said first end;

positioning means mounted about said longitudinal member intermediate said first and second ends;

driving means at said second end and adapted to engage a device for applying a known torque force;

whereby inserting said first end of said longitudinal member through a first outer stage of blades and into the interior of the turbine such that said positioning means abuts said first outer stage of blades to place said means for applying a separating force between two adjacent blades of an interior stage of blades, and applying a rotary force to said tool acts to separate said adjacent blades, the measure of the magnitude of the force required to separate the blades serving as an indication of outer shroud notch wear.

The present invention also includes the method of measuring outer shroud notch wear comprising the steps of:

providing means for applying a separating force between two adjacent turbine blades;

positioning said means for applying a separating force between two adjacent blades in a fully assembled turbine adjacent said outer shroud;

applying a torque force to said means for providing a separating force to force apart said adjacent blades;

measuring said torque force to determine an indication of outer shroud notch wear; and repeating the above steps at several different positions around the circular array of blades.

BRIEF DESCRIPTION OF THE DRAWINGS

The apparatus of the present invention is shown by way of example in the accompanying drawings in which.

DESCRIPTION OF THE PREFERRED EMBODIMENTS

Figure 1:
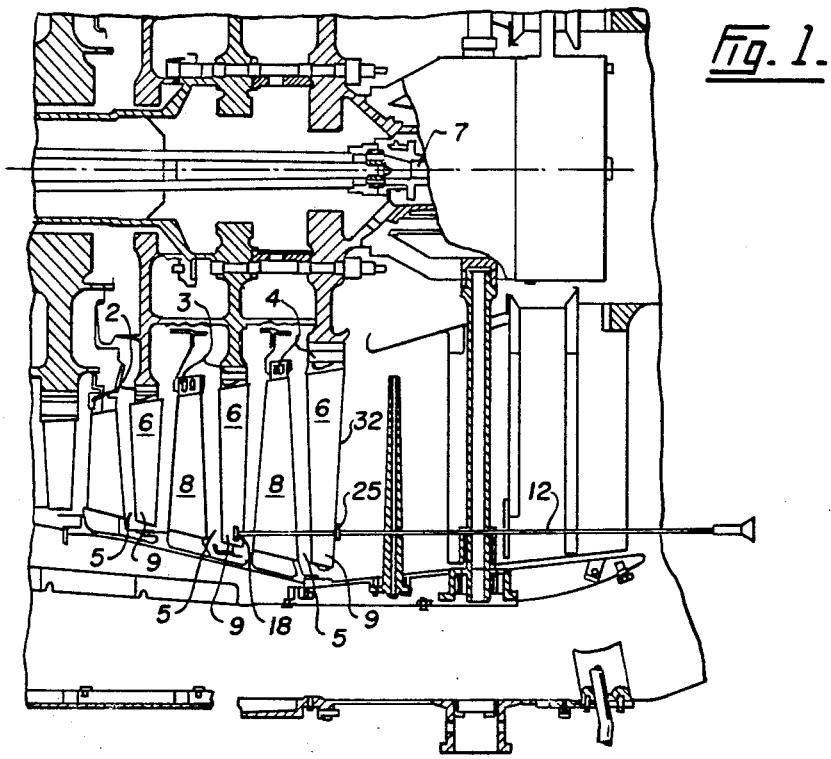
FIG. 1 is a section view through a JT8D turbine showing the tool in use.

Referring to FIG. 1, there is shown a cross-section through a typical jet engine turbine, in this case, a Pratt & Whitney JT8D engine. There are a plurality of turbine stages 5, each stage including a circular array of blades 6 arranged about a rotatable main shaft 7. Associated with each set of blades 6 are sets of stationary vanes 8 that the blades rotate between. In FIG. 1, there are 3 stages shown: fourth stage blades and vanes 4, third stage blades and vanes 3 and second stage blades and vanes 2.

Figure 2:
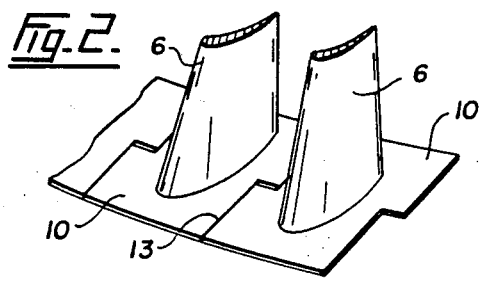
FIG. 2 is a pictorial view showing the turbine blade outer shroud arrangement.

As best shown in FIG. 2, each turbine blade 6 is formed at its outer end 9 into a shroud portion 10. The shroud portions of the each blade interfit to form a tight annulus that surrounds each stage of turbine blades. The shroud portions are shaped to interfit along a shroud notch 13. With use, it is these notches that become worn leading to flexing of the turbine blades 6 which can result in failure of one or more blades. Particularly in Pratt & Whitney JT8D jet engines, it is the third stage turbine blade outer shroud notches that are susceptible to wear.

The tool of the present application is designed to allow for measurement of outer shroud notch wear in a turbine without requiring dismantling of the turbine as is presently the case.

Figure 3:
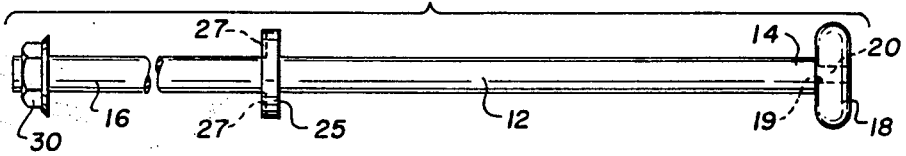
FIG. 3 is an elevation view of the tool.
Figure 4:
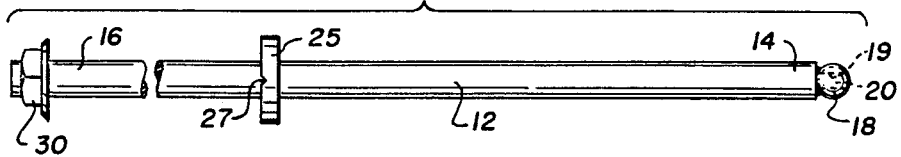
FIG. 4 is a plan view of the tool.

Referring to FIGS. 3 and 4, the tool comprises a longitudinal member 12 having first and second ends 14 and 16 respectively. Preferably, longitudinal member 12 is a forth inch diameter steel rod. For use in the JT8D engine, member 12 is 20 inches long.

Adjacent first end 14 there is attached means for applying a separating force between two adjacent turbine blades comprising a gauge pin 18 welded across the end of the longitudinal member to form a "T". For use in the JT8D engine, pin 18 is preferably a cylindrical member one forth inch in diameter and 0.9 inches in length. The pin is rounded at both ends and has a central hole 19 drilled across the width of the cylinder. First end 14 is formed with a projection 20 and gauge pin 18 is pinned onto this projection. Pin 18 is also welded to the longitudinal member to ensure it is firmly attached.

Positioning means are mounted on longitudinal member 12 intermediate ends 14 and 16. In the illustrated embodiment, the positioning means comprises a disc 25 having a central hole through which the longitudinal member is fitted. For use in a JT8D engine, the disc is three forths inches in diameter is located 3.880 inches from gauge pin 18. Preferably, the face of disc 25 facing toward second end 16 is formed with a groove 27 across a diameter of the disc intersecting the central hole through the disc. This groove is aligned with gauge pin 18 and is filled with white paint or a similar easily visible material and provides an indication of the rotational angle of the tool.

At second end 16, there is mounted driving means comprising a hexagonal nut 30. Nut 30 is engageable by a standard drive socket of a torque wrench or other torque measuring or torque limiting tool. Alternatively, longitudinal member 12 can be formed from a piece of hexagonal bar. If appropriate, the section of the tool between gauge pin 18 and disc 25 is be machined down such that the section is sufficiently narrow to be inserted between the blades and vanes of a turbine.

Referring to FIG. 1, the tool is used in the following manner on a fully assembled Pratt & Whitney JT8D engine:

First end 14 is inserted through the fourth stage blades and vanes 4 adjacent the outer shroud location until disc 25 of the positioning means abuts the rear or trailing edges 32 of the fourth stage blades. Disc 25 is positioned on longitudinal member 12 such that when the disc abuts the fourth stage blades, gauge pin 18 is positioned between a pair of adjacent third stage blades. Gauge pin 18 is initially introduced between the blades in a radially aligned positioned so that it does not contact the blades. Groove 27 on disc 25 provides an indication of the angle of the gauge pin once the gauge pin disappears behind the fourth stage blades and vanes.

Obviously, the distance between disc 25 and gauge pin 18 can be adjusted in order to measure shroud wear in other stages of blades or in different engines that space apart the stages differently. As long as the rear or trailing edge of the foremost stage of blades is used as a reference point, positioning the gauge pin between the appropriate stage of blades is easily accomplished.

In the present example, once the gauge pin is in place between a pair of adjacent third stage blades a torque measuring or torque limiting device such as a torque wrench or a torque limiting screw driver is applied to hexagonal nut 30 which protrudes from the rear of the engine. The tool is rotated through 180 degrees thereby causing the rounded ends of gauge pin 18 to engage and force apart the adjacent third stage turbine blades. The shroud notches 13 adjacent the turbine blades being forced apart are likewise forced apart. A measure of the force required to rotate the tool through 180 degrees is taken. If the blade shroud notches are unworn, considerable torque will be required to rotate the tool. If notch wear has occurred, the torque required to rotate the tool will be less. A relationship between the torque required to rotate the tool between two adjacent blades and the degree of wear on the blade outer shroud notches must be previously established. Once known, this relationship can be used to determine outer shroud blade notch wear simply by measuring the torque required to rotate the tool. The above procedure is repeated at several positions around the turbine to gauge the accumulated wear on all 92 of the third stage turbine blades.

The tool and method of the present invention allow the jet engines being tested to be examined while in place on the aircraft without disassembly. Engines can remain safely in service under periodic monitoring using the present apparatus and method until a normally scheduled shop visit or until the tool and method indicate that blade notch wear is excessive and corrective shop action is required. This procedure thereby avoids the expensive, time consuming and unnecessary operation of disassembly and examination of the turbine blades when outer shroud notch wear is within acceptable limits.

Although the present invention has been described in some detail by way of example for purposes of clarity and understanding, it will be apparent that certain changes and modifications may be practiced within the scope of the appended claims.

I claim:

1. A tool for measuring turbine blade outer shroud notch wear in situ in a turbine having multiple stages of turbine blades, each stage being arranged in a circular array comprising:
   a longitudinal member having first and second ends;
   means for applying a separating force between two adjacent turbine blades at said first end;
   positioning means mounted about said longitudinal member intermediate said first and second ends;
   driving means at said second end;
   whereby inserting said first end of said longitudinal member through a first outer stage of blades and into the interior of the turbine such that said positioning means abuts said first outer stage of blades to place said means for applying a separating force between two adjacent blades of an interior stage of blades, and applying a torque force to said tool acts to separate said adjacent blades, the measure of the magnitude of the force required to separate the blades serving as an indication of outer shroud notch wear.

2. A tool as claimed in claim 1 in which said means for applying a separating force comprises a gauge pin mounted at right angles to said longitudinal member at said first end.

3. A tool as claimed in claim 1 in which said positioning means comprises a disc through which said longitudinal member extends, said disc being spaced away from said first end of said longitudinal member such that when said disc abuts the outer stage of blades, said means for applying a separating force is positioned between two adjacent blades of an interior stage of blades.

4. A tool as claimed in claim 3 in which said positioning means is marked to indicate the angle of rotation of the device.

5. A tool as claimed in claim 1 in which said driving means comprises a hexagonal nut mounted to said second end.

6. A tool as claimed in claim 1 in which said longitudinal member is formed from a hexagonal bar and said driving means is said second end of said longitudinal bar.

7. A method for measuring outer shroud notch wear in place in a turbine having stages of turbine blades arranged in a circular array comprising the steps of:

providing means for applying a separating force between two adjacent turbine blades;

positioning said means for applying a separating force between two adjacent blades in a fully assembled turbine adjacent said outer shroud;

applying a torque force to said means for providing a separating force and rotating said means through 180 degrees to force apart said adjacent blades;

measuring said torque force to determine an indication of outer shroud notch wear; and repeating the above steps at several different positions around the circular array of blades.

8. A method as claimed in claim 7 including the step of relating the torque force exerted to a pre-determined relationship establishing the wear on the blade outer shroud notch for a given torque force.

9. A method as claimed in claim 7 in which said means for applying a separating force between two adjacent blades comprises:

a longitudinal member having first and second ends;

means for applying a separating force between two adjacent turbine blades at said first end;

positioning means mounted about said longitudinal member intermediate said first and second ends; and driving means at said second end.

* * * * *